United States Patent

Jacobs

[11] Patent Number: 6,074,361
[45] Date of Patent: *Jun. 13, 2000

[54] CATHETER

[76] Inventor: Clemens Josephus Jacobs, Veenlanden 40, 3871 Rd., Hoevelaken, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/945,491

[22] PCT Filed: Apr. 19, 1996

[86] PCT No.: PCT/NL96/00174

§ 371 Date: Oct. 20, 1997

§ 102(e) Date: Oct. 20, 1997

[87] PCT Pub. No.: WO96/32980

PCT Pub. Date: Oct. 24, 1996

[30] Foreign Application Priority Data

Apr. 20, 1995 [NL] Netherlands ............................ 1000183

[51] Int. Cl.[7] ............................ A61M 37/00; A61M 5/00; A61M 25/00; A61M 25/01

[52] U.S. Cl. ............................ 604/95; 604/264; 604/528; 604/523

[58] Field of Search ............................ 604/95, 264, 281, 604/528, 523; 600/143, 146, 433, 434, 435; 128/772

[56] References Cited

U.S. PATENT DOCUMENTS 3,605,725  9/1971  Bentov .

FOREIGN PATENT DOCUMENTS 43 33 090   3/1995  Germany .
WO 95/03742 2/1995  WIPO .

*Primary Examiner*—Ronald Stright
*Assistant Examiner*—Michael J. Hayes
*Attorney, Agent, or Firm*—Quarles & Brady LLP

[57] ABSTRACT

A description is given of a catheter (1) which comprises at least one flexible tubular catheter body (2) with a proximal end and a distal end, and an element interacting with the tubular catheter body, which element produces bending or stretching of the distal end by means of axial movement. Said element comprises a rigid shaping wire (4) with a predetermined intrinsic shape of at least the distal end, which wire is accommodated in the tubular body (2) and is slidable back and forth inside the tubular catheter body (2). The distal end of tubular catheter body (2) also has a predetermined intrinsic shape. An axial movement of the shaping wire (4) produces a specific change of shape in at least the distal end of the tubular catheter body (2), the specific shape being determined by the intrinsic shape of the shaping wire when it is present in the distal end, or by the intrinsic shape of the tubular catheter body (2) in the absence of the shaping wire (4).

6 Claims, 4 Drawing Sheets

CATHETER

The invention relates to a catheter of the type according to the preamble of claim 1, such as is disclosed by WO 92/14506. The wall of said catheter contains two wire-type elements which lie diametrically opposite each other and are slidable in the lengthwise direction, one being an elastic element which can assume both a curved and a straight shape, and the other being a 'stretch' element which has the tendency to prevent the elastic element from assuming the curved shape. Both elements run on into the distal end of the tubular catheter body. Axial movement of one of the elements causes the elastic element to deform from one to the other shape, and the distal end of the tubular catheter body is curved or stretched accordingly.

The structure of this catheter is complicated by the presence of the two elements, while its use, which requires not only manipulation of the catheter but also the operation of two further elements, is difficult. In addition, the free cross section of the lumen is limited by the presence of these two elements, which is a disadvantage if the catheter is being used for diagnostic purposes, for example for the introduction of contrast liquid.

The object of the invention is to overcome these disadvantages. This is achieved with a catheter of the type described in the characterizing part of claim 1.

The catheter according to the present invention, which has only one shaping wire, therefore has two "boundary shapes", that of the shaping wire and that of the catheter body. When the shaping wire has been pushed near to the distal end of the catheter body, the more flexible catheter body will assume the shape of the shaping wire. However, when the shaping wire is pushed back in the direction of the proximal end of the catheter, the catheter body will assume its predetermined intrinsic shape. By "intrinsic shape" we mean here the shape which the distal end of the catheter body assumes when the shaping wire has been removed and the catheter body is free of any other influence of any kind.

By using a shaping wire of—curved—intrinsic shape, or a tubular catheter body of different—curved—intrinsic shape, it is possible to obtain a change in the working shape of the catheter.

The "boundary shapes" of the catheter can be determined depending on the desired application, and "intermediate shapes" are, of course, also usable.

In particular, the distal end of the shaping wire is such a shape that it is suitable for linking up the right coronary artery.

The distal end of the catheter in this case is slightly curved in such a way that the catheter can easily be pushed by way of an artery into the right coronary artery of a patient.

The distal end of the catheter body is preferably shaped in such a way that it is suitable for linking up the left coronary artery.

The reason for this measure is as follows: the shape of the distal end of the catheter which is suitable for linking up the left coronary artery differs, as is known, from the shape which is suitable for linking up in the right coronary artery, in that the distal end of the former is a much more curved shape. The curve of this shape is such that a catheter with this shape of distal end cannot be introduced as such by way of one of the arteries into the body of the patient.

Until now, in heart catheterization it has been customary for the above mentioned linking-up to use a feed wire inserted into the body almost to the aortic arch. A catheter with a specific shape of distal end, a shape corresponding to that of, for example, the right coronary artery, is then pushed along the feed wire until the distal end has reached the desired place, and a contrast liquid is introduced into the coronary artery concerned by way of the catheter. After this action, the catheter is removed from the patient's body. In order also to introduce contrast liquid into the other coronary artery, i.e. the left one in this case, a catheter with a specific shape of distal end, a shape corresponding to that of the left coronary artery, is again inserted into the patient's body along a feed wire. This method therefore requires the insertion of the feed wire twice, and the insertion of a catheter twice is very onerous for the patient and exposes the latter to X-rays during a relatively long period.

A catheter of the above mentioned type makes it possible to introduce contrast liquid into both the right and the left coronary artery in one operation, without changing catheter bodies.

To this end, the catheter is first of all inserted into the right coronary artery with the shaping wire fully slid in, and contrast liquid is introduced at this point by way of the catheter. The catheter is subsequently moved over a short distance out of the right coronary artery, and the shaping wire is slid back so that the distal end of the catheter body assumes the shape of the left coronary artery. During the deformation of the distal end the catheter is now pushed into the left coronary artery, and contrast liquid is then introduced at this point. After the contrast liquid has been introduced, the catheter is returned to its original state by sliding in the shaping wire again, and the catheter is removed from the patient's body. The intermediate shapes assumed by the distal end of the catheter are such that with them the catheter can also be linked into any coronary bypass vein which may be present.

A further advantageous embodiment of the catheter according to the present invention is described in subclaim 4.

The invention will be explained in greater detail below with reference to the appended drawing, in which.

Figure 1:
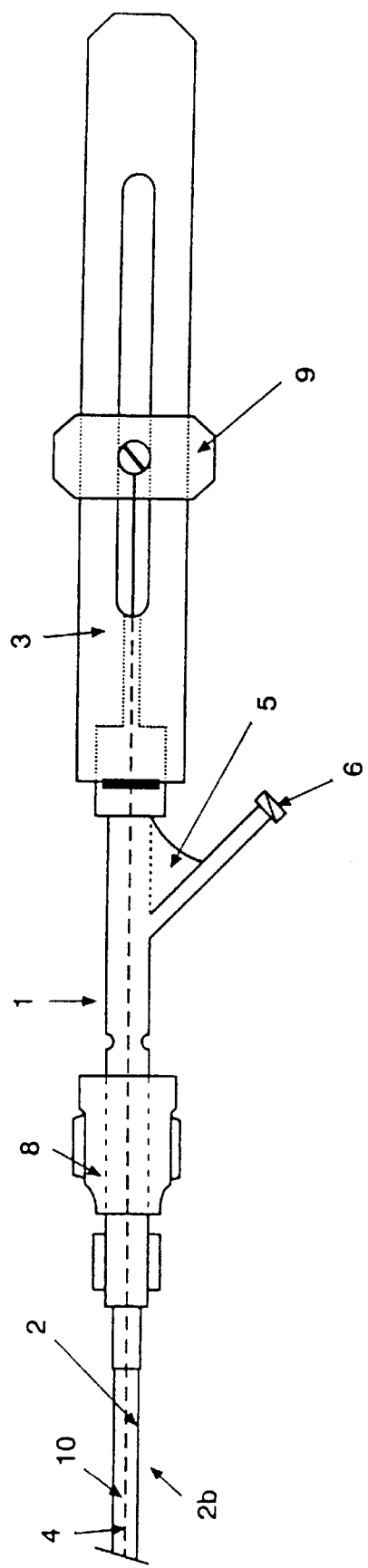
FIG. 1 shows diagrammatically and partially in section a side view of the catheter according to the invention.

FIG. 1 shows a catheter 1 according to the invention. The catheter 1 comprises a flexible tubular catheter body 2 with a distal end 2a and a proximal end 2b. The catheter body 2 is made of a synthetic resin, such as, for example, nylon, polyethylene or polyurethane. The catheter body 2 contains a relatively rigid shaping wire 4. Said shaping wire 4 can be made of stainless steel, and is preferably coated with a layer of Teflon®, in order to prevent red blood cells from accumulating on the metal and thereby causing thrombosis. The inner lumen 10 of the catheter body 2 is large enough for a suitable quantity of contrast liquid to pass through.

The proximal end of the tubular catheter body 2 interacts with a control element, comprising a handle 3 in which a sliding element 9 is accommodated. In the embodiment shown in FIG. 1 a known so-called Y-connector 5, provided with a supply aperture or infusion port 6, is situated between the catheter body and the control element 3. Reference number 8 indicates a connecting element which connects the tubular catheter body 2 to the Y-connector 5.

Figure 2:
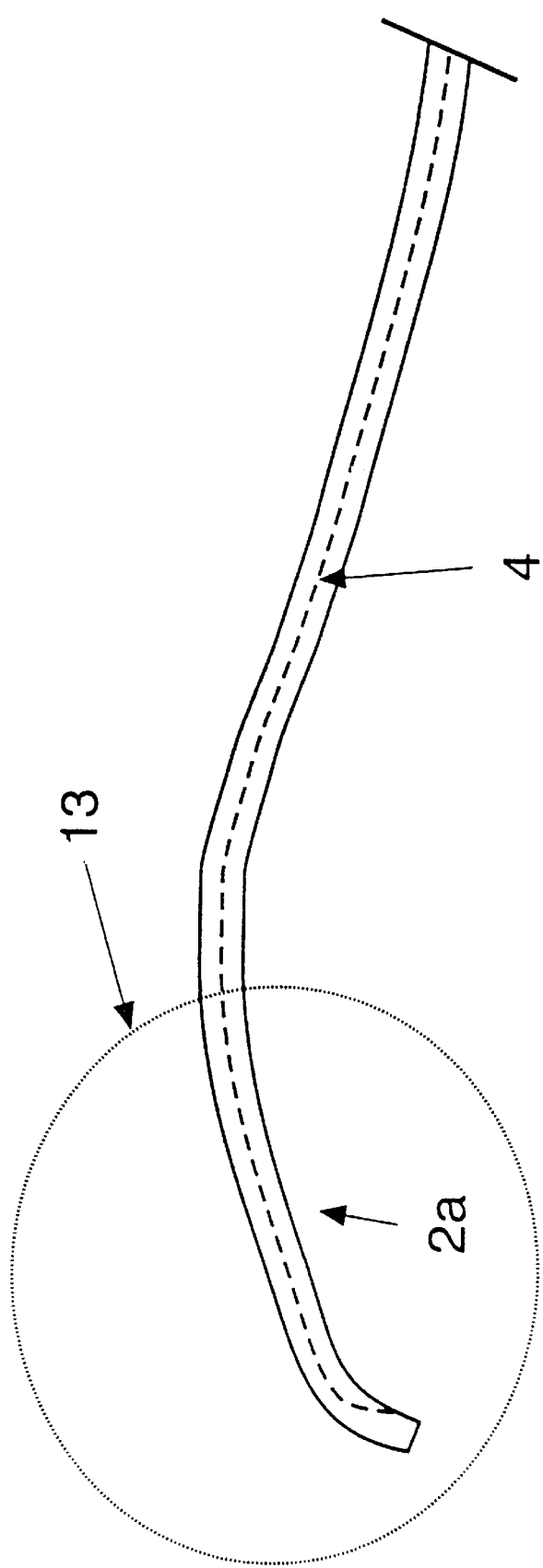
FIG. 2 shows diagrammatically a section of the distal end of the catheter in a first embodiment.

As said above, the shaping wire 4 runs through the catheter body 2 and is attached by its proximal end to the sliding element 9. When the sliding element 9 is slid up to the Y-connector 5, the distal end of the shaping wire 4 will be situated at the same, or virtually the same, position as the distal end of the tubular catheter body 2. The shape of the catheter body, which is relatively more flexible than the shaping wire, is then determined by the shape of the shaping wire 4. This situation is shown in FIG. 2; the shape of the distal end of the catheter shown there, indicated by reference number 13, is then the same as the intrinsic shape of the shaping wire and is suitable for linking up the right coronary artery. In this shape the catheter can also be inserted into the body of the patient. The predetermined intrinsic shape of the shaping wire is shown in FIG. 3.

Figure 4:
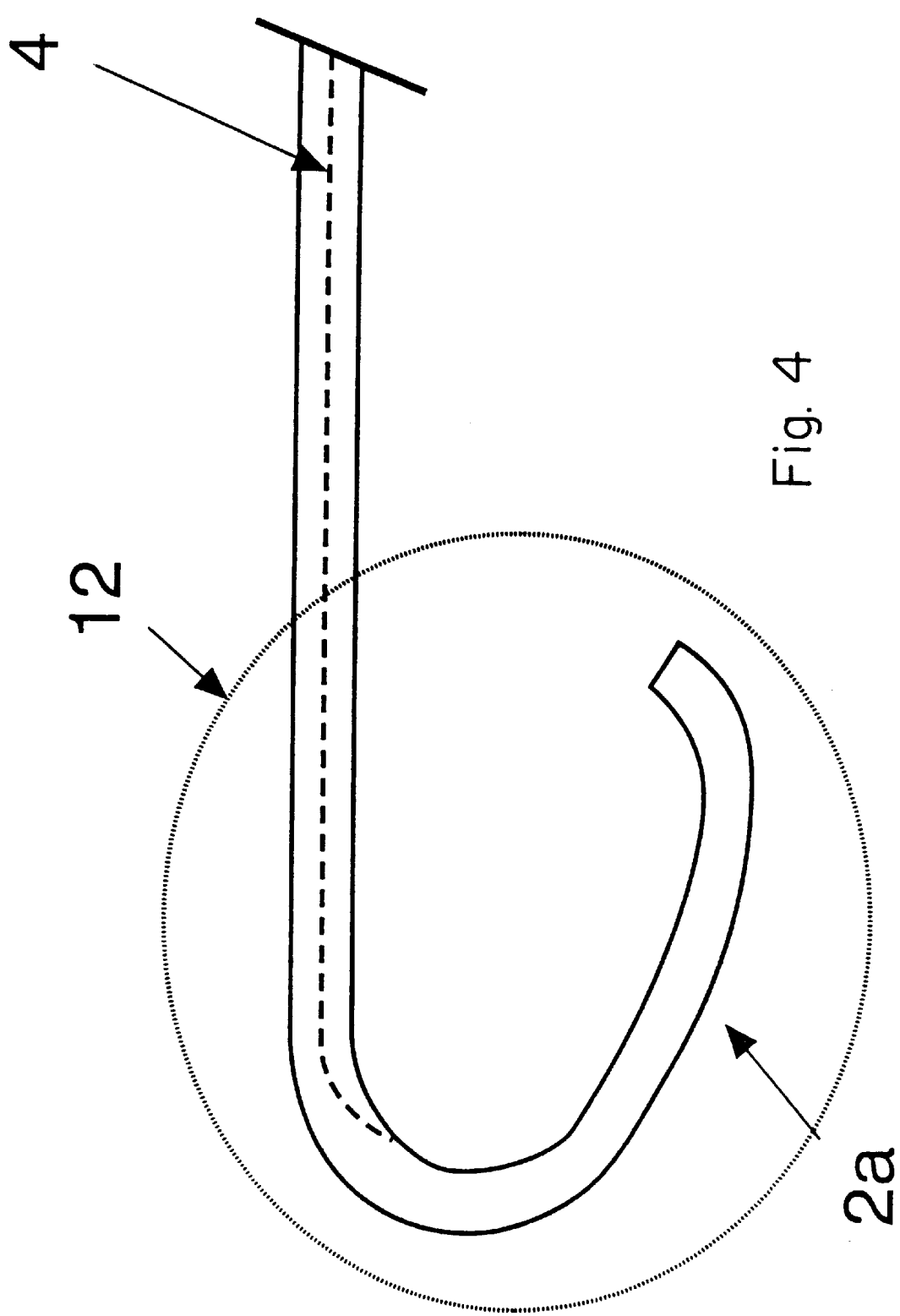
FIG. 4 shows diagrammatically a section of the distal end of the catheter in a second embodiment.

When the sliding element 9 is slid away from the Y-connector 5, the shaping wire 4 is also slid back, and the catheter body 2 assumes its predetermined intrinsic shape again. This situation is shown in FIG. 4, and the shape shown, indicated by reference number 12, is suitable for linking up the left coronary artery. However, in this shape the catheter cannot be introduced into the patient's body.

When the sliding element 9 is moved the distal end of the tubular catheter body 2 assumes a number of intermediate shapes, which also make the catheter suitable for linking into a coronary bypass vein.

Figure 3:
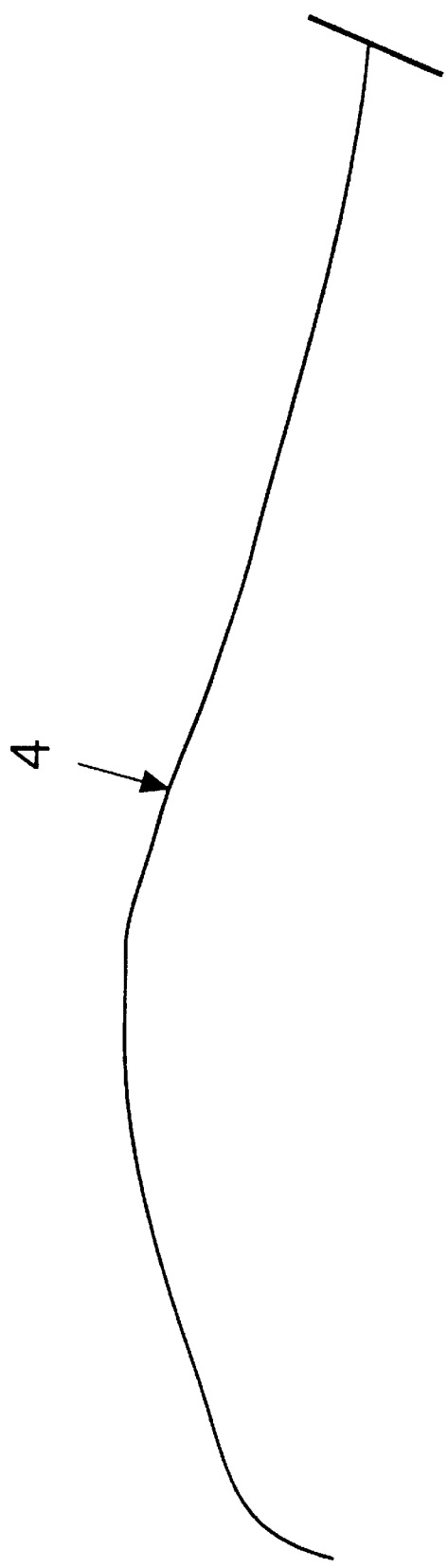
FIG. 3 shows the predetermined intrinsic shape of the shaping wire.

When the catheter according to the present invention is being used for diagnostic purposes, the catheter 1 with a shape of distal end which is shown in FIG. 3 is inserted by way of the femoral artery into the patient's body up to the right coronary artery. If desired, it is also possible first to insert a feed wire up to the aortic arch, and then to slide the catheter along the feed wire. However, the use of a feed wire is not necessary when the catheter according to the present invention is used. After the insertion of the catheter 1, a contrast liquid is introduced through the infusion port 6. The catheter 1 is then withdrawn a short distance from the right coronary artery and moved into the left coronary artery, while the shaping wire 4 is pulled by means of the sliding element 9 out of the distal end of the tubular catheter body 2, and the catheter body 2 assumes its intrinsic shape, which is suitable for linking up the left coronary artery. After the introduction of contrast liquid into the left coronary artery, while the catheter is being withdrawn, the sliding element 9 is moved in the direction of the Y-connection 5, so that the catheter 1 can be moved in its initial state out of the patient's body again. If a coronary bypass vein is present, the catheter 1 can also be used for the introduction of contrast liquid at this point.

What is claimed is:

1. Controllable catheter comprising:
   a rigid shaping wire having a portion thereof with a predetermined curved intrinsic shape; and,
   a flexible tubular catheter body enclosing said shaping wire, said catheter body having a distal end and a proximal end, said distal end changeable between a relaxed and a tensioned boundary shape, said boundary shapes being curved and determined by axial movement of said shaping wire, wherein
   said distal end having said tensioned boundary shape when said portion of said shaping wire axially inserted into said distal end, and
   said distal end having said relaxed boundary shape when said portion of said shaping wire axially retracted from said distal end.

2. Catheter according to claim 1, wherein said tensioned shape of said distal end is suitable for linking up a right coronary artery.

3. Catheter according to claim 1, wherein said relaxed shape of said distal end is suitable for linking up the left coronary artery.

4. A controllable catheter, comprising:
   a flexible tubular catheter body having a distal end and a proximal end, said distal end having a first predetermined curved intrinsic shape; and,
   a rigid shaping wire completely enclosed by said catheter body, a portion of said wire interacting with said distal end for tensioning said distal end by controlled axial movement of said wire, said portion of said wire having a second predetermined curved intrinsic shape;
   said distal end changeable between two shapes, wherein axial movement of said shaping wire relative to said distal end changes the shape of said distal end, the shape of said distal end having said second curved intrinsic shape when said shaping wire interacts with said distal end and having said first curved intrinsic shape when said shaping wire is not interacting with said distal end.

5. A catheter according to claim 4, wherein the second curved intrinsic shape is suitable for linking up with a right coronary artery.

6. A catheter according to claim 4, wherein the first curved intrinsic shape is suitable for linking up with a left coronary artery.

\* \* \* \* \*